(12) United States Patent
Eytan et al.

(10) Patent No.: US 6,661,508 B2
(45) Date of Patent: Dec. 9, 2003

(54) INSPECTION SYSTEMS USING SENSOR ARRAY AND DOUBLE THRESHOLD ARRANGEMENT

(75) Inventors: Giora Eytan, Rechovot (IL); Sagie Tsadka, Yavne (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/212,041

(22) Filed: Aug. 6, 2002

(65) Prior Publication Data

US 2002/0186367 A1 Dec. 12, 2002

Related U.S. Application Data

(62) Division of application No. 09/410,848, filed on Oct. 1, 1999, now Pat. No. 6,496,256.

(51) Int. Cl.[7] .............................................. G01N 21/00
(52) U.S. Cl. .................................................... 356/237.5
(58) Field of Search ........................... 356/237.1–237.5; 250/552.41, 563, 572

(56) References Cited

U.S. PATENT DOCUMENTS

| 4,501,439 A | 2/1985 | Antes |
| 5,648,653 A | 7/1997 | Sakamoto et al. |
| 6,084,664 A | 7/2000 | Matsumoto et al. |

*Primary Examiner*—Michael P. Stafira
(74) *Attorney, Agent, or Firm*—Sughrue Mion LLP.

(57) ABSTRACT

A two dimensional sensor array is used to collect light diffracted from the inspected substrate. The signal generated by each individual sensor is passed through a threshold. Those signals which are below the threshold are amplified and are summed up. The summed signal is then passed through a second threshold. Summed signals which pass the second threshold are flagged as indicating suspect locations on the substrate. In the preferred embodiment, the entire circuitry is provided in the form of a CMOS camera which is placed in the Fourier plane of the diffracted light.

18 Claims, 3 Drawing Sheets

INSPECTION SYSTEMS USING SENSOR ARRAY AND DOUBLE THRESHOLD ARRANGEMENT

This is a divisional of application Ser. No. 09/410,848, filed Oct. 1, 1999 now U.S. Pat. No. 6,496,256; the disclosure of which is incorporated herein by reference.

FIELD OF THE INVENTION

This invention relates to systems for inspection of substrates, especially semiconductor wafers and reticles. More specifically, the invention relates to a novel system which utilizes a sensor array in conjunction with two threshold arrangement, preferably integrated on a CMOS camera.

BACKGROUND OF THE INVENTION

Several systems are known in the art for the inspection of wafers and reticles. Three examples of such systems that are currently available on the market are depicted in FIGS. 1–3. In the system exemplified in FIG. 1, the wafer 100 is illuminated with a light beam emanating from a light source 110 and reaching the wafer at a 90° angle (generally referred to as normal illumination). Preferably, light source 110 provides coherent light, i.e., source 110 may be a laser source. The light beam is scanned over the wafer by a scanner 120, typically an acousto-optical deflector (AOD) or a rotating mirror, in the direction marked by the double-headed arrow. The wafer 100 is moved in the perpendicular direction by moving the stage upon which the wafer rests. Thus, a two dimensional area of the wafer can be scanned by the light beam.

Since the wafer has basically a mirror-like top surface, the light beam is specularly reflected back per Snell's law at 180°. This specularly reflected light is collected by a light sensor 140 and its signal is used to obtain a "bright field" image, i.e., an image created from specularly reflected light. However, whenever the light beam hits an irregularity on the wafer, such as a particle, the light scatters in various directions. Some of the diffracted/scattered light is then collected by the light sensors 130, and their signal is used to obtain a "dark field" image, i.e., an image created from diffracted/scattered light. Thus, irregularities appear in the dark field image as stars in a dark sky.

In the system exemplified in FIG. 2, the wafer 200 is illuminated by a light beam emanating from light source 210, but reaching the wafer at a shallow angle, generally referred to as grazing illumination. The light beam is scanned over the wafer by a scanner 220, typically an acousto-optical scanner or a rotating mirror, in the direction marked by the double-headed arrow. The wafer 200 is moved in the perpendicular direction by moving the stage upon which the wafer rests. Thus, a two dimensional area of the wafer can be scanned by the light beam.

Since the light reaches the wafer at a grazing angle θ, its specular reflection is at a corresponding angle, θ', according to Snell's law. This light is collected by sensor 240, and its signal is used to create the bright field image. Any scattered light is collected by sensors 230, the signal of which is used to create dark field images.

It should be appreciated that in the above exemplified systems, with respect to each sensor the image data is acquired serially. That is, each two dimensional image, whether bright or dark field, is constructed by acquiring signals of pixel after pixel, per the scanned light beam. This is time consuming serial operation, which directly affects the throughput of such systems. Moreover, the scan speed of such systems is limited by the scanner's speed (i.e., the band-width for an acousto-optic scanner) and by the electronics that support the detectors, e.g., the PMT (Photo-Multiplier Tube). Thus, a need exists to develop a system that does not utilize a scanned light beam.

Another difficulty with systems which use coherent light is diffraction caused by features arranged in a repeated order, thereby effectively forming a grating. Specifically, in semiconductor devices many features are constructed in a repeated order fashion. When these features are illuminated by a coherent light beam, they diffract the light in much the same manner as a diffraction grating would diffract the light. However, such constructive diffraction can be mistaken by the system for a defect. One way to overcome such a problem is to use a spatial filter in the Fourier plane, as exemplified by filters 235 in FIG. 2. This problem and proposed solutions are disclosed in, for example, U.S. Pat. No. 4,898,471, 4,806,774, and 5,276,498, which are incorporated herein by reference.

The system depicted in FIG. 3 performs a bright field inspection only, but does not use a scanner to scan the light beam. Instead, light source 310 provides a relatively broader light beam which illuminates the wafer 300 with a relatively large spot 315. A TDI sensor is used to image an elongated strip 325 of the illuminated spot. The length of the strip corresponds to the width of the TDI sensor. For example, if the TDI sensor comprises a 2048×2048 pixels, then the scanned strip is of size 2048×1. As the wafer is moved by the stage, strips are imaged and collected to form a bright field two-dimensional image of the inspected area.

Looking forward, as design rules shrink, the importance of detecting increasingly small irregularities becomes paramount. With design rules such as 0.18 and 0.15 $\mu$m, very small irregularities, such as particles of sub-micron size, can be killer defects and cause the device to malfunction. However, in order to detect such small irregularities, one needs to use a very small wavelength light source, such as ultra violate (UV) or deep ultra violate (DUV) light source. This presents at least two crucial problems: first, optical elements operating in the DUV regime are expensive and, second, small short wave implies small spot size of the light beam; thus, the scanning speed and collection data rate need to be increased.

The small size of killer defects also present a formidable challenge for bright field system which do not use scanning, such as the TDI system depicted in FIG. 3. Specifically, since bright field system construct an actual image of the inspected area, the image includes multitude of structural elements built upon the wafer. Thus, the resulting image looks much like a maze, and it is increasingly difficult to detect a small irregularity in the maze-like image. Thus, the system requires a complicated image processing algorithm to recognize the defect, thereby increasing the processing power and time required and increasing the cost of purchasing and operating the system. It is not clear at this time whether even the most sophisticated algorithm may be unable to detect such small irregularities.

SUMMARY OF THE INVENTION

According to the present invention, a two dimensional sensor array is used to collect light returned from the inspected substrate. The signal generated by each individual sensor is passed through a threshold. Those signals which are below the threshold are amplified and are summed up. The summed signal is then passed through a second threshold. Summed signals which pass the second threshold are flagged as indicating suspect locations on the substrate.

The preferred implementation of the present invention is an integrated CMOS camera. Specifically, both thresholds, the amplifiers and the adder are integrated into the CMOS camera. This implementation is advantageous in that it enables much faster throughput of the system.

DETAILED DESCRIPTION OF THE PREFERRED EMBODIMENT

Before, proceeding with the description of the preferred embodiments, it should be noted that any of the embodiments are suitable for inspection of un-patterned wafers. However, several notable advantages of the invention are particularly useful for the more complicated task of patterned wafers inspection. Therefore, much of the discussion presented herein relates to patterned wafers.

Figure 1:
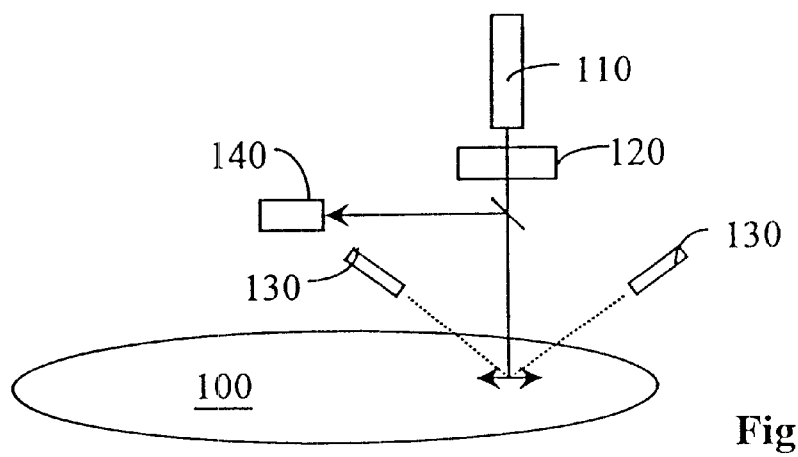
FIG. 1 is a schematic representation of prior art wafer inspection system using normal illumination.
Figure 2:
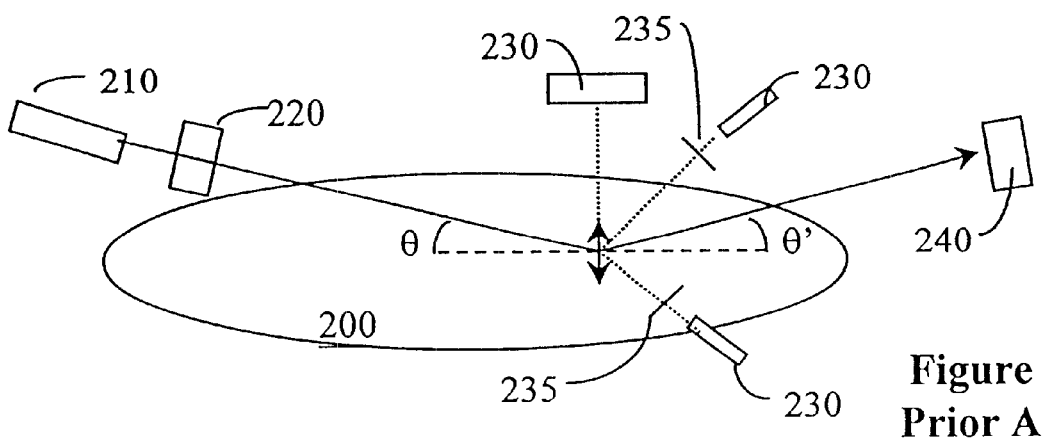
FIG. 2 is a schematic representation of another prior art wafer inspection system, using grazing angle illumination.
Figure 3:
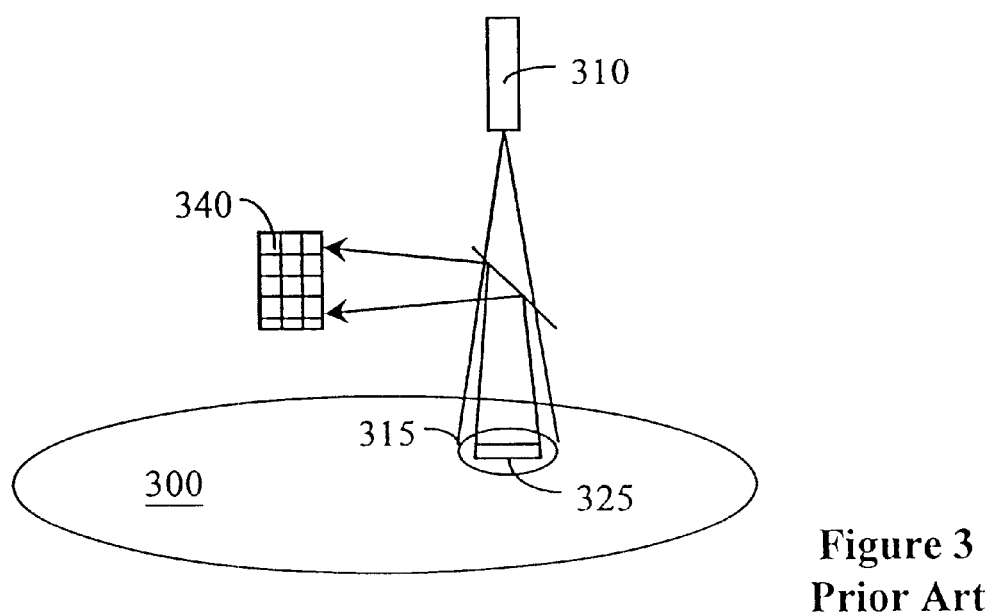
FIG. 3 is a schematic representation of another prior art wafer inspection system using a TDI sensor.
Figure 4:
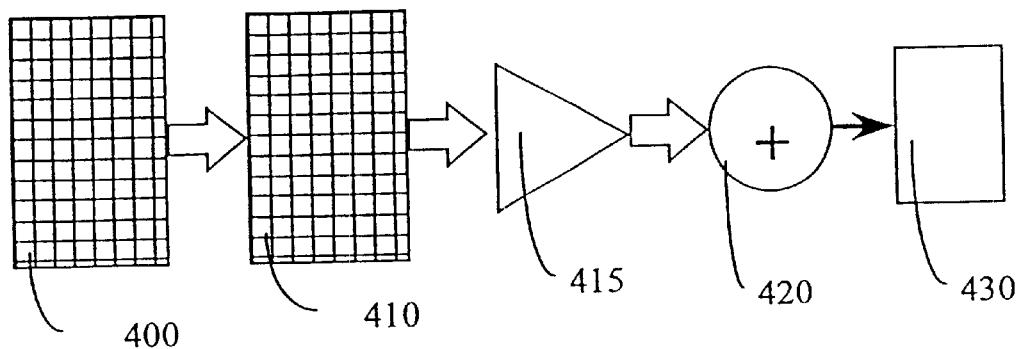
FIG. 4 is block diagram of an embodiment of the present invention.

FIG. 4 depicts a simplified block diagram of the present invention. A two-dimensional sensor array 400 is positioned in the Fourier plane of the scattered/diffracted light. The array receives light scattered from the wafer (not shown), and each of the sensors provides a signal corresponding to the level of light it senses. The signal from each of the sensors in sensor array 400 is passed through a threshold 410. This threshold is set relatively high. Specifically, since the array is placed in the Fourier plane, it is anticipated that constructive diffraction will take place so that high intensity spots will be created in the Fourier plane. In order to avoid confusing such scattering as being defects, these spots are removed.

Figure 5:
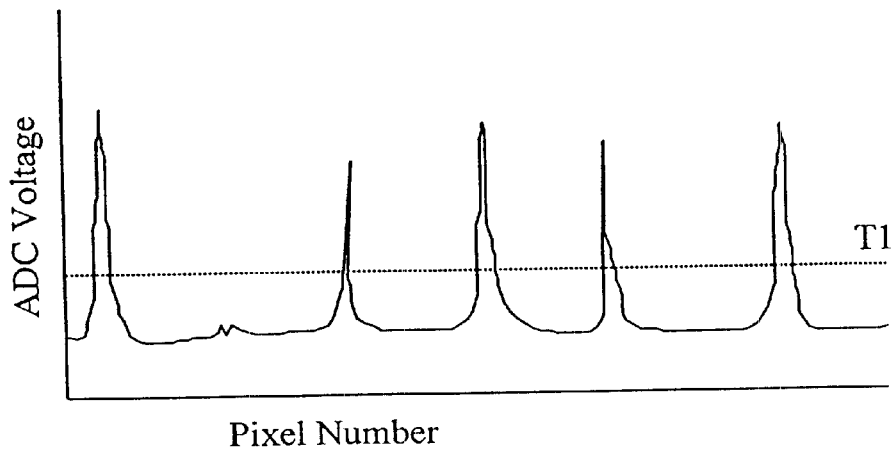
FIG. 5 exemplifies signal obtained from a line of sensor elements.

To understand this better, the reader's attention is directed to FIG. 5, exemplifying the signal collected from a strip of pixels. As can be seen, the signal consists of background level and several high peaks. As can be understood, the peaks are the result of constructive diffraction of ordered features. Thus, a threshold T1 is set to eliminate the signal from pixels receiving such bright light; thus eliminating the need for a spatial filter.

On the other hand, light diffracted from singularities, such as random particles on the wafer is distributed rather evenly across all the pixels in the array. (The scatter pattern depends on the wavelength used and the shape and size of the particles, but in any case it will not be summed up to a single point on the Fourier plane.) Therefore, when a defect is present on the wafer, all the pixels will receive an augmented amount of light at a somewhat even distribution.

To identify whether the signal from the array indicates the presence of a defect, the signals which are below the threshold T1 are passed, amplified by amplifier 415, and then summed up by adder 420. It should be appreciated, that while amplifier 415 is not a necessary element for the invention to function, it provides a better conditioned signal for processing. The summed signal is then applied to a second threshold 430. The second threshold is a rather low threshold. Basically, it is set to identify the amount of light which is above normal background light. This, of course, will have to be adjusted by the user depending on the particular wafer and layer under inspection. That is, some wafers and layers will have higher background noise than others, so the threshold must be adjusted accordingly. If the summed signal is above the threshold 430, the inspected location is flagged as being suspect of having a defect thereupon.

In the preferred embodiment, the arrangement depicted in FIG. 4 is implemented on a single semiconductor device. Such devices are generally known as CMOS cameras. These devices basically include a face surface which is divided into pixels and is sensitive to light, and a backing which is basically electronic circuitry designed for the particular purpose the camera is used for. Thus, current suppliers are capable of providing such CMOS cameras with a circuit tailored to the customer's specifications. For more information on CMOS cameras and manufacturers, the reader is referred to: www.vvl.co.uk; www.imec.be; www.neuricam.com; and www.dep.nl.

One particular advantage of using a CMOS camera is its parallel nature. That is, regular two dimentional CCD's have a limited number of taps, each tap providing data of several pixels in a serial manner. Such processing would make the inspection system very slow. Therefore, it is preferred to use the CMOS camera so that all the pixels can be processed at once. Additionally, since the main hardware, e.g., thresholds and amplifiers can be built right into the CMOS camera, processing speed is further enhanced.

A notable feature of the invention is the combination of CMOS camera placed at the Fourier plane. This structure eliminates the need for a spatial filters since the camera itself serves the function of a filter. Moreover, when the camera functions as a filter, the filter is dynamic. One problem with prior art systems is that their spatial filter is static, i.e., one filter is prepared for each design of inspected article and a new filter needs to be created for each new article. Also, the orientation of the filter prohibits rotational and spatial misalignment of the article with respect to the filter. On the other hand, using the dynamic filter feature of the invention, the filter shape can change every sampling period to fit exactly to the inspected article and its orientation. Consequently, no spatial or rotational alignment is dictated by the filter and new filter shapes can be created "on the fly" during inspection.

Another feature of the invention is that the level of the first threshold, i.e., the Fourier threshold, can be dynamically changed so that the filter's sensitivity can be changed in real time. This is a tramendous advnacement over current spatial filters which do not have sensitivity adjustments.

Figure 6:
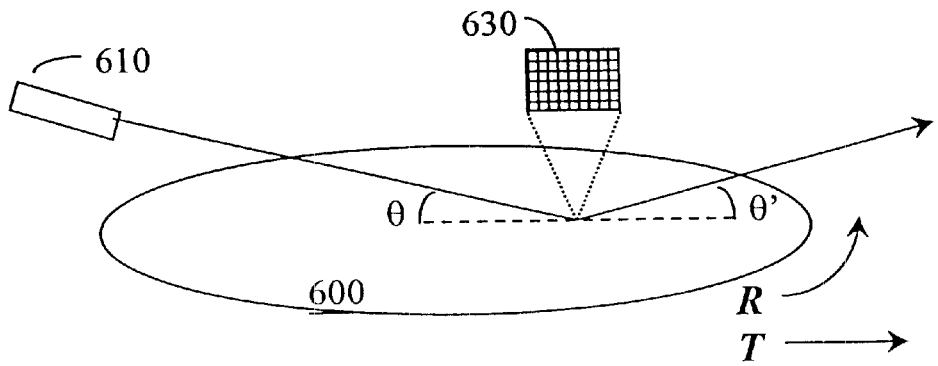
FIG. 6 depicts an embodiment of the invention using the detection scheme of FIG. 4.

A system embodiment of the invention is exemplified in FIG. 6. A wafer stage is provided which rotates the wafer (shown by Arrow R), while also translating it in one direction (shown by arrow 7). A light source 610, preferable a coherent light source, such as a laser, provide illuminating beam which impinges the wafer at a grazing angle. The rotation and translation of the wafer are designed so that the illumination spot traces the entire wafer.

A sensor array 630 is provided in the Fourier plane to collect scattered light. As explained above, light scattered from ordered features is constructively added up in the Fourier plane and, therefore, will appear as bright spots on the array 630. On the other hand, light scattered from singularities, such as a particle, will be diffracted somewhat evenly on all the sensors of the array. Using the two thresholds in the manner described above, the scattering from singularities can be distinguished from the scattering from ordered features.

Figure 7:
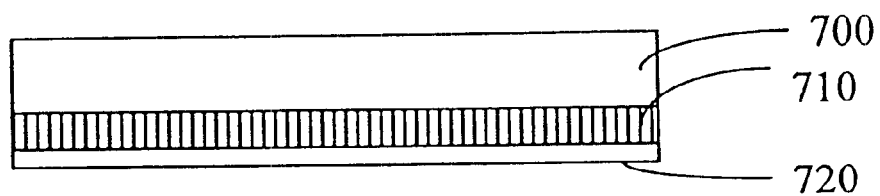
FIG. 7 exemplifies a CMOS camera having an image intensifier provided on its light receiving side.

In a further embodiment of the invention, exemplified in FIG. 7, an image intensifier is provided in front of the CMOS camera. Such intensifiers are usually used on night vision CCD's and can be obtained from, e.g., www.dep.nl. In FIG. 7, layer 700 is the CMOS camera and layer 720 is the image intensifier layer. Fibers layer 710 connects between intensifier layer 720 and CMOS camera layer 700. As is known, when a photon hits the intensifier layer 720, it causes the layer to emit several photons. These photons are collected by the fibers and are detected by the CMOS camera elements. Thus, faint light signal is intensified before it is detected by the CMOS camera.

According to a further embodiment, the responsiveness of the system is increased by using a CMOS detector having its active pixel elements of avalanche photo-diodes (APD) with internal gain. Such CMOS cameras have programmable internal gain for each pixel, so as to provide increase sensitivity for low light applications, while maintaining high spatial resolution and bandwidth of conventional CMOS detectors. More information about this detection technology can be found a www.csem.ch. See also, A. Biber and P. Seitz, Avalanche Photodetection in CMOS, Proc. SPIE, 3410, 1998, 10; and P. Seitz, The Smart Image Sensor Toolbox for Automotive Vision Applications, Advanced Microsystems for Automotive Applications, 98 Eds. D. E. Ricken and W. Gessner, Springer, Berlin, 1998, 123. Such a sensor can be used in all of the system embodiments exemplified herein.

Figure 8:
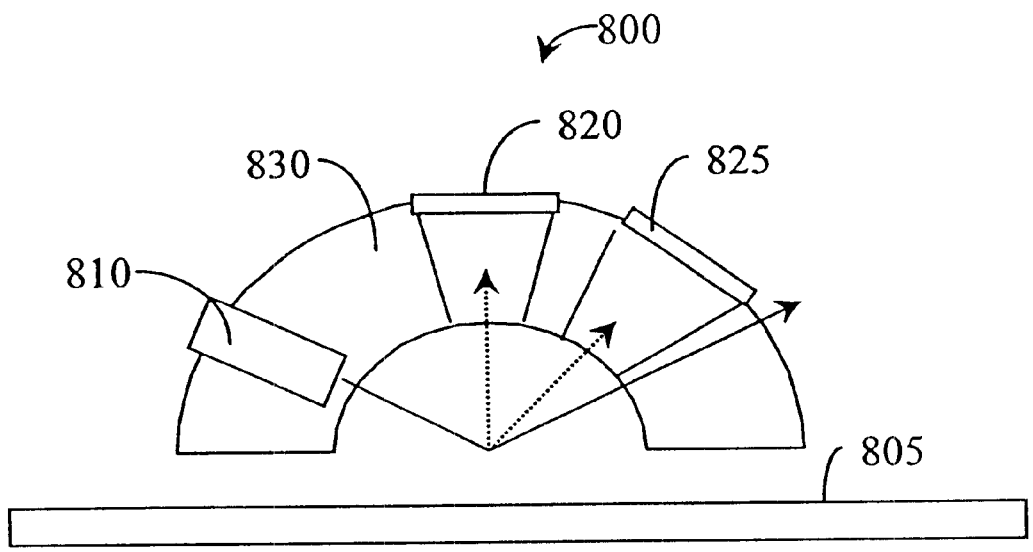
FIG. 8 depicts an embodiment of a detection head according to the present invention.

FIG. 8 depicts a head assembly 800 according to an embodiment of the invention. The head assembly is particularly suitable for inspection of substrates, such as semiconductor wafers and photolithography masks. The head assembly 800 comprises a housing structure 830 which houses a light beam source 810, such as a laser diode assembly. In the depicted embodiment, the laser beam is at an oblique angle to the surface of the inspected substrate 805. Ordinarily, the light would be reflected at a corresponding oblique angle, as shown by the solid arrow. One CMOS camera, 820, is provided at normal angle to the substrate, detecting light scattered at a normal angle, as shown by the broken arrow. Another CMOS camera, 825, is provided at an oblique angle and positioned to detect light scattered at an oblique angle from the substrate. Both CMOS cameras 820 and 825 are positioned at the Fourier plane, as explained above. It should be appreciated that, while not specifically shown, appropriate optical elements may be used to properly focus the light.

While embodiments of the invention have been described by way of illustration, it will be apparent that the invention can be carried into practice with many modifications, variations and adaptations without departing from the scope and spirit of the invention, as defined by the appended claims.

For example, while the stage of the preferred embodiment provides a rotation-translation motion, a conventional x-y stage can be used instead. However, some advantages of the rotating stage are that it avoids the need for a scanner, such as an AOD, and it allows for a smaller footprint of the entire system. Similarly, while the system of the preferred embodiment is constructed in the form of a CMOS camera, one may use a line or two-dimensional CCD coupled to the appropriate hardware to provide the threshold analysis. Of course, the threshold analysis may also be implemented using appropriate software. However, using the CMOS camera implementation provides the most compact solution with the highest throughput, since no algorithm calculations needs to be performed.

What is claimed is:

1. A system for inspection of substrates, comprising:
    a stage supporting the substrate, said stage rotating and translating the substrate in one direction;
    a light source providing a light beam illuminating a spot on the substrate at a grazing angle;
    a sensor array having a plurality of sensors thereon and positioned at a Fourier plane above the substrate to receive light scattered from the spot;
    a circuitry receiving signals from the sensor array and determining whether the signals indicate presence of a singularity on the substrate.

2. The system according to claim 1, wherein said circuitry comprises:
    a filter receiving signal from each of the plurality of sensors, and blocking any signal which is above a first threshold;
    an adder receiving and adding signals that pass the first filter to provided an added signal; and;
    a comparator comparing the added signal to a second threshold and issuing a singularity indication if the added signal is above the second threshold.

3. The system of claim 2, wherein said sensor array and said circuitry are integrally formed on a single substrate.

4. The system of claim 2, wherein said sensor array and said circuitry are integrally formed as a CMOS camera.

5. The system according to claim 1, wherein the sensor array comprises a CMOS camera incorporating active pixel elements of avalanche photo-diodes (APD).

6. The system of claim 4, further comprising an image intensifier situated in front of said CMOS camera.

7. The system of claim 4, further comprising a housing assembly housing said light source and CMOS camera.

8. The system according to claim 4, wherein said CMOS camera comprises active pixel elements of avalanche photo-diodes (APD).

9. A system for inspection of substances, comprising:
    a stage supporting the substrate;
    a light source illuminating a spot on the substrate;
    a scanning mechanism providing a relative motion between the substrate and the spot so as to cause the spot to scan the substrate;
    a sensor array comprising a plurality of sensors and being disposed to collect light scattered from the spot;
    a filter receiving a signal from each of the plurality of sensors, and blocking any signal which is above a first threshold;
    an adder receiving and adding signals that pass the filter to provided an added signal; and;
    a comparator comparing the added signal to a second threshold and issuing a singularity indication if the added signal is above the second threshold.

10. The system of claim 9, wherein said sensor array, filter, adder and comparator are integrally constructed on a single substrate.

11. The system of claim 9, wherein said sensor, filter, adder and comparator are integrally constructed as a CMOS camera.

12. The system of claim 9, wherein said stage is a turntable stage.

13. The system of claim 9, wherein said sensor array is position in the Fourier plane of light diffracted from the spot.

14. The system of claim 9, wherein said scanning mechanism linearly translates the rotating stage.

15. The system according to claim 9, wherein the sensor array comprises a CMOS camera incorporating active pixel elements of avalanche photo-diodes (APD).

16. The system for inspection of substrates as recited in claim 9 wherein said filter is dynamically changeable in real time.

17. The system for inspection of substrates as recited in claim 9, wherein said filter is a Fourier filter.

18. A method for inspection of substrates, comprising:
illuminating a spot on the substrate with a light beam;
collecting light diffracted from the spot, by placing a sensor array at the Fourier plane of the diffracted light;
comparing output of each sensor from the sensor array to a first threshold;
adding up all the outputs that are lower than the first threshold to provide an added signal;
comparing the added signal to a second threshold; and
announcing a defect when the added signal is above the second threshold.

* * * * *